(12) United States Patent
Hamada et al.

(10) Patent No.: US 8,088,094 B2
(45) Date of Patent: Jan. 3, 2012

(54) PLANNING METHOD AND APPARATUS FOR PERITONEAL DIALYSIS AND HEMODIALYSIS HYBRID REMEDY

(75) Inventors: Hiroyuki Hamada, Fukuoka (JP); Masahiro Okamoto, Fukuoka (JP)

(73) Assignee: JMS Co., Ltd., Hiroshima (JP)

( * ) Notice: Subject to any disclaimer, the term of this patent is extended or adjusted under 35 U.S.C. 154(b) by 0 days.

(21) Appl. No.: 12/570,109

(22) Filed: Sep. 30, 2009

(65) Prior Publication Data

US 2010/0042331 A1 Feb. 18, 2010

Related U.S. Application Data

(62) Division of application No. 10/555,701, filed as application No. PCT/JP2004/006863 on May 14, 2004.

(30) Foreign Application Priority Data

May 14, 2003 (JP) .................................. 2003-136067
Aug. 4, 2003 (JP) .................................. 2003-205819

(51) Int. Cl.
*A61M 1/00* (2006.01)

(52) U.S. Cl. .......... 604/29; 210/646; 210/647; 700/271; 424/520

(58) Field of Classification Search .................... 604/29; 210/646–647; 700/271; 424/520
See application file for complete search history.

(56) References Cited

U.S. PATENT DOCUMENTS

| 5,518,623 | A | 5/1996 | Keshaviah et al. |
| 6,691,040 | B2 | 2/2004 | Bosetto et al. |
| 2001/0004523 | A1* | 6/2001 | Bosetto et al. ............... 435/4 |
| 2002/0075227 | A1* | 6/2002 | Miller et al. ................. 345/156 |

FOREIGN PATENT DOCUMENTS

| JP | 2000-140100 | 5/2000 |
| JP | 2001-218837 | 8/2001 |

OTHER PUBLICATIONS

Vonesh et al., Peritoneal dialysis kinetic modeling validation in a multicenter clinical study, 1996, International Society for Peritoneal Dialysis, Peritoneal Dialysis International, vol. 16, pp. 471-481.*
Kawanishi et al., Hemodialysis together with peritoneal dialysis is one of the simplest ways to maintain adequacy in continuous ambulatory peritoneal dialysis, Adv. Perir. Dial. 1999, 15, pp. 127-131.*
Hamada et al., Validation of a new analytical model for peritoneal transport model using rabbit in vivo experimental data, 2000, Nephrology, 5, pp. 59-64.*
Koichi Uchiyama et al., "Shukan Creatinine Jokyoryo o Mochii Ketsueki Toseki Fukumaku Toseki Heiyo Ryohoji no Tekisei Toseki Chiryo Keikaku o Okonatta 2 Rei" Journal of Japanese Society for Dialysis Therapy, Jan. 2003, vol. 36, No. 1, pp. 73-79.

(Continued)

*Primary Examiner* — In Suk Bullock
*Assistant Examiner* — Robert Eom
(74) *Attorney, Agent, or Firm* — Wenderoth, Lind & Ponack, L.L.P.

(57) ABSTRACT

The present invention is a peritoneal dialysis and hemodialysis hybrid-remedy planning method using an index that is shared by both peritoneal dialysis and hemodialysis and indicates an effect of dialysis. To be specific, the index is $M/C(0)/V_B$, which is obtained by dividing a ratio $M/C(0)$—where $M$ is a removal amount of a solute for a fixed time period, and $C(0)$ is a concentration of the solute in blood before the dialysis—by a patient's body fluid volume, $V_B$. The present invention is capable of representing the dialysis effect of PD and HD as an integrated sum, achieving concise and explicit PD and HD hybrid-remedy planning.

9 Claims, 17 Drawing Sheets

OTHER PUBLICATIONS

Akiyasu Yamashita, "Ketsueki Joka no Kiso 27 Fukumaku Toseki ni Ketsueki Toseki o Heiyo suru Ketsueki Jokaho (I)", the Japanese journal of clinical dialysis, Sep. 2000, vol. 16, No. 11, pp. 1817 to 1821.

Akiyasu Yamashita, Seminar Urea kinetik modeling Nyumon, Kidney and dialysis, Oct. 2002, vol. 53, separate vol. (October), pp. 56 to 59.

Akiyasu Yamashita, "PD-HD Heiyo Ryoho o Kangaeru Part 03 PD+hd Ryoho no Koritsu (1) Kiso o Shirimasho", the Japanese journal of dialysis & caring, Sep. 2001, vol. 7, No. 9, pp. 882-886.

"Ketsueki Jyouka (Blood Purification)", Kanehara Publishing, Nov. 30, 1990, pp. 14-15 (along with partial English translation).

International Search Report Report (in English language) issued Aug. 24, 2004 in PCT/JP2004/006863 of which the parent of the present application is the U.S. National Stage.

* cited by examiner

FIG.2 SEQUENCE OF PD-HD HYBRID-REMEDY PLANNING PROGRAM

FIG.4

PERITONEAL FUNCTION TESTING PROTOCOL

| TIME | DIALYSIS SOLUTION | | | | SAMPLING | | | REMARKS |
|---|---|---|---|---|---|---|---|---|
| hr | OSMOTIC PRESSURE | RETENTION PERIOD | DRAINED FLUID VOLUME | WATER REMOVAL VOLUME | BLOOD SAMPLING | URINE SAMPLING | URINE VOLUME (URINE COLLECTION) | |
| 13 | LOW | 6hr | → | → | | → | | |
| 14 | | | | | | | | |
| 15 | | | | | | | | |
| 16 | | | | | | | | |
| 17 | | | | | | | | |
| 18 | | | | | | | | |
| 19 | | | D1 | VDL1 | | | | |
| 20 | LOW | 3hr | → | → | | | | |
| 21 | | | | | | | | |
| 22 | | | | | | | | |
| 23 | | | D2 | VDL2 | | | | |
| 24 | MEDIUM | 8hr | → | → | | | | NIGHTTIME |
| 1 | | | | | | | | |
| 2 | | | | | | | | |
| 3 | | | | | | | | |
| 4 | | | | | | | | |
| 5 | | | | | | | | |
| 6 | | | | | | | | |
| 7 | | | | | | | | |
| 8 | | | D3 | VDM1 | | | | |
| 9 | MEDIUM | 4hr | D4 → | → | | | | PET like |
| 10 | | | D5 → | | | | | |
| 11 | | | | | | | | |
| 12 | | | | | | | | |
| 13 | | | D6 | VDM2 | B1 | U1 | VU | |

MEASUREMENT TARGETS

| SOLUTION | DIALYSIS SOLUTION | BLOOD | URINE |
|---|---|---|---|
| UREA NITROGEN | ○ | ○ | ○ |
| CREATININE | ○ | ○ | ○ |

FIG.5

INPUT DATA

| PATIENT INFORMATION | SEX | HEIGHT | WEIGHT |
|---|---|---|---|
| REMARKS | ○ | ○ | ○ |

| PD | SAMPLE | UREA | CREATININE | WATER REMOVAL VOLUME | RETENTION PERIOD |
|---|---|---|---|---|---|
| | D1 | ○ | ○ | ○ | ○ |
| | D2 | ○ | ○ | ○ | ○ |
| | D3 | ○ | ○ | | |
| | D4 | ○ | ○ | | |
| | D5 | ○ | ○ | | |
| | D6 | | ○ | ○ | ○ |
| | B1 | ○ | ○ | | |

| HD | | UREA | CREATININE | | DIALYSIS DURATION |
|---|---|---|---|---|---|
| | CLEARANCE | ○ | ○ | | |
| | DIALYSIS DURATION | | | | |
| | DIALYSIS SOLUTION VOLUME | | | | |

| URINE | | UREA | CREATININE | URINE VOLUME | DURATION |
|---|---|---|---|---|---|
| | U1 | ○ | ○ | ○ | ○ |

OUTPUT DATA

| BASIC PARAMETER | |
|---|---|
| TOTAL BODY FLUID VOLUME (TBF Vol.) | BODY SURFACE AREA (BSA) |
| | Index |

| DYNAMIC PARAMETER | Index |
|---|---|
| MTAC | M/C(O) |
| a1,a2,a3 | |
| VD0 | |
| G | |
| TIME-LAPSE CHANGES OF SOLUTE CONCENTRATION IN BLOOD | |

| DYNAMIC PARAMETER | Index |
|---|---|
| TOTAL BODY FLUID VOLUME (TBF Vol.) | M/C(O) |

| DYNAMIC PARAMETER | Index |
|---|---|
| RESIDUAL RENAL FUNCTION (RRF) | M/C(O) |

FIG.6

CLINICAL DATA INPUT SCREEN

| MENU | Input Clinical Data |
|---|---|
| CLINICAL DATA INPUT | |
| DRAINED-FLUID-VOLUME CURVE CREATION | |
| D/P CURVE CREATION | |
| ANALYSIS RESULTS | |
| END | |
| help | |

PATIENT INFORMATION
⦿ MALE   ○ FEMALE
HEIGHT = 159.5 cm    WEIGHT = 58.1 kg

RENAL FUNCTION
URINE VOLUME = 170.0 mL
UREA NITROGEN CONCENTRATION = 41.0 mg/dL
CREATININE CONCENTRATION = 12.0 mg/dL

HD CONDITIONS
UREA NITROGEN CL = 170.0 mL/min
CREATININE CL = 150.0 mL/min
DIALYSIS DURATION = 240.0 min
WATER REMOVAL VOLUME = 2000.0 mL

PD CONDITIONS
INJECTED SOLUTION VOLUME = 2000.0 mL

| | UREA NITROGEN mg/dl | CREATININE mg/dl | DRAINED FLUID VOLUME ml | RETENTION PERIOD min |
|---|---|---|---|---|
| D1 | 70.0 | 11.0 | 2090.0 | 360 |
| D2 | 55.0 | 6.5 | 2190.0 | 180 |
| D3 | 73.0 | 13.4 | 2280.0 | 500 |
| D4 | 9.0 | 1.0 | | 1 |
| D5 | 48.0 | 7.2 | | 120 |
| D6 | 67.0 | 10.0 | 2350.0 | 240 |
| B1 | 74.0 | 14.0 | | |

Update    Initialize    Back

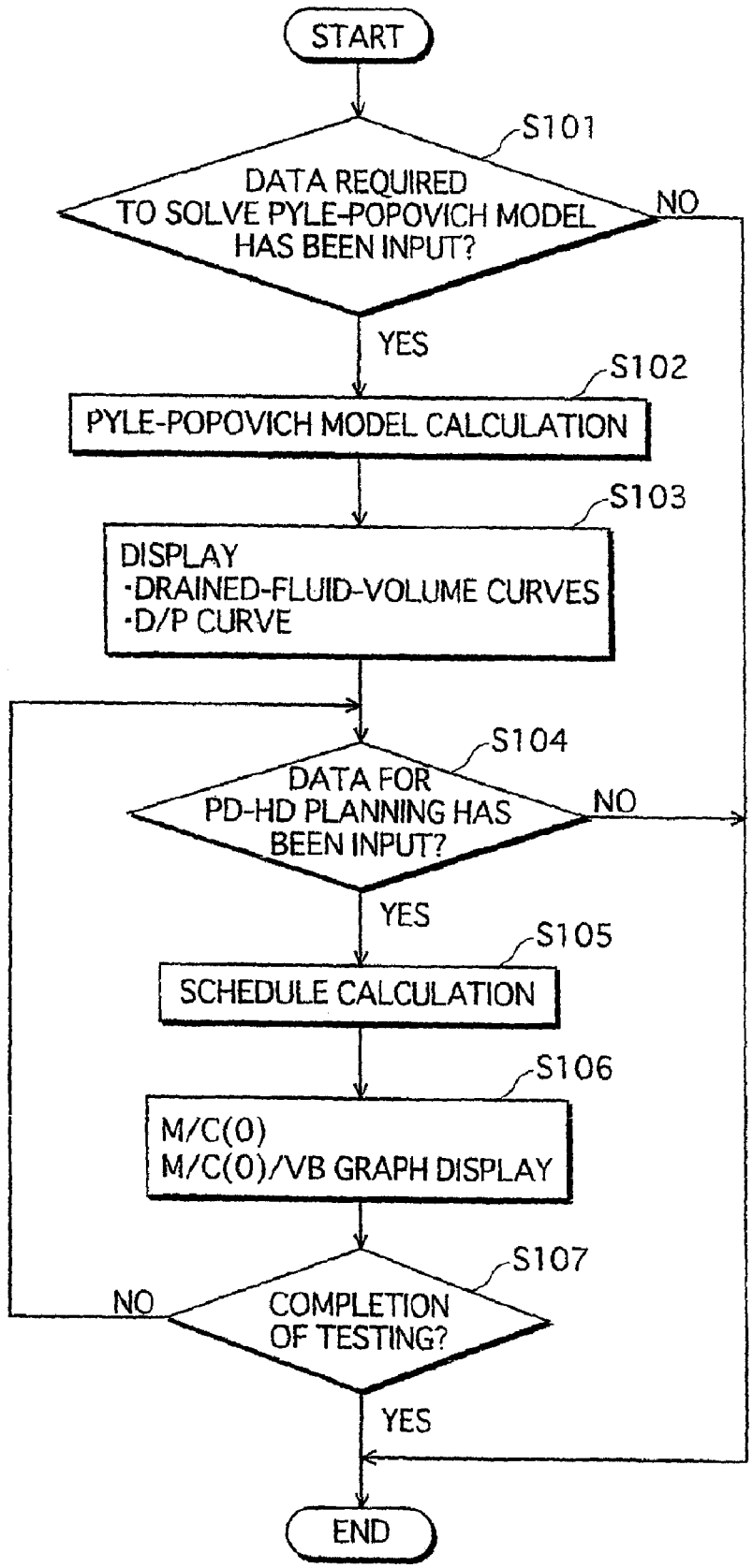

FIG. 8

SCREEN OF ANALYSIS RESULTS OF DATA FOR CREATING DRAINED-FLUID-VOLUME CURVES

Analysis of PD Fluid Removal

PATIENT INFORMATION

| BODY SURFACE AREA | BODY FLUID VOLUME | INJECTED SOLUTION VOLUME | RESIDUAL SOLUTION VOLUME |
|---|---|---|---|
| 1.62 m² | 32428.9 mL | 2000.0 mL | 161.3 mL |

WATER REMOVAL PARAMETER

| | a1 ml/min | a2 1/min | a3 ml/min |
|---|---|---|---|
| LOW-OSMOTIC-PRESSURE DIALYSIS SOLUTION | 7.41 | -0.0250 | -0.574 |
| MEDIUM-OSMOTIC-PRESSURE DIALYSIS SOLUTION | 10.41 | -0.0250 | -0.273 |

Analysis  Time Course  Back

MENU
CLINICAL DATA INPUT
DRAINED-FLUID-VOLUME CURVE CREATION
D/P CURVE CREATION
ANALYSIS RESULTS
END help

FIG. 10

SCREEN OF ANALYSIS RESULTS OF DATA FOR CREATING D/P CURVE

| MENU |
|---|
| CLINICAL DATA INPUT |
| DRAINED-FLUID-VOLUME CURVE CREATION |
| D/P CURVE CREATION |
| ANALYSIS RESULTS |
| END |

Analysis of PD Solute Removal

PARAMETER ESTIMATION METHOD
⦿ OPTIMIZATION  ○ SIMPLE(1 pool model)

PATIENT INFORMATION

| | UREA NITROGEN | CREATININE |
|---|---|---|
| PRODUCTION RATE | 4.15 | 0.648 |
| | mg/min | |

DYNAMIC PARAMETER

| | DIALYSIS SOLUTION (OSMOTIC PRESSURE) | MTAC mL/min | REFLECTION COEFFICIENT [—] |
|---|---|---|---|
| ○ UREA NITROGEN | LOW OSMOTIC PRESSURE | 14.83 | 0.233 |
| ○ CREATININE | LOW OSMOTIC PRESSURE | 6.75 | 0.312 |
| ○ UREA NITROGEN | MEDIUM OSMOTIC PRESSURE | 17.16 | 0.191 |
| ⦿ CREATININE | MEDIUM OSMOTIC PRESSURE | 12.35 | 0.271 |

[Analysis]   [Time Course]   [Back]

[help]

FIG.12 PD-HD PLAN INPUT SCREEN

Simulation of the PD+HD Hybrid Treatment

PD-HD HYBRID-REMEDY SCHEDULE

|  | M | Tu | W | Th | F | Sa | Su |
|---|---|---|---|---|---|---|---|
| PD | ● | ● | ● | ● | ● | ○ | ○ |
| HD | ○ | ○ | ○ | ○ | ○ | ● | ○ |
| Rest | ○ | ○ | ○ | ○ | ○ | ○ | ● |

PD PLAN

| # | DIALYSIS SOLUTION | ID Vol | DT |
|---|---|---|---|
| 1 | 360 | 2000.0 | 360 |
| 2 | 360 | 2000.0 | 360 |
| 3 | 360 | 2000.0 | 360 |

DYALYSIS SOLUTION TYPE
4 | 360 ▼ |  ID Vol. 2000 mL   RETENTION PERIOD 360 min

EXCHANGES 4 ▼ TIMES

Update    Erase

HD PLAN

| DIALYSIS DURATION min | WATER REMOVAL VOLUME mL | UN_CL mL/min | Cr_CL mL/min |
|---|---|---|---|
| 240 | 2000.0 | 170.0 | 150.0 |

Estimation    PET    Time Course    Back

MENU
CLINICAL DATA INPUT
DRAINED-FLUID-VOLUME CURVE CREATION
D/P CURVE CREATION
ANALYSIS RESULTS
END
help

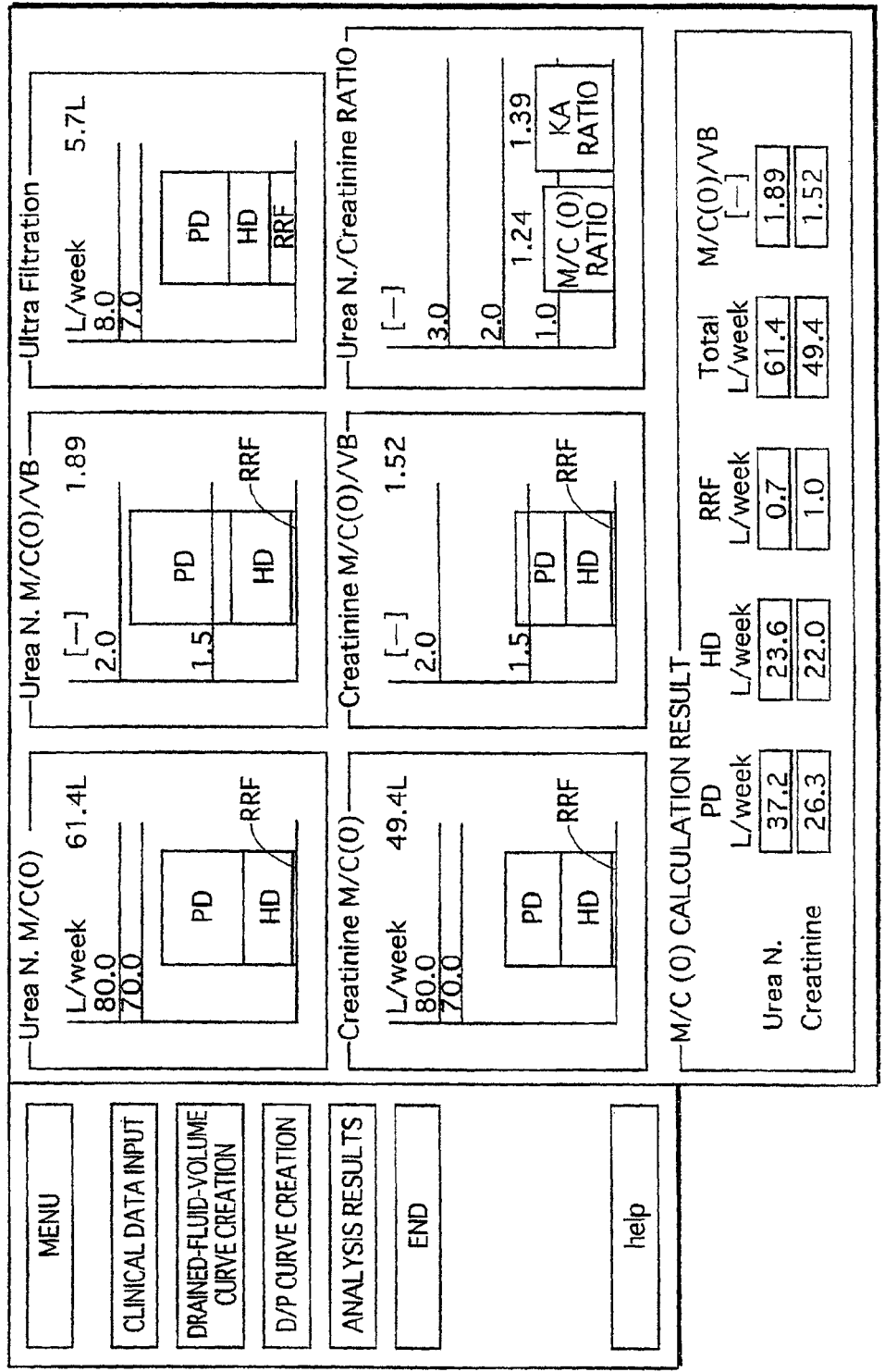
FIG.13 PD-HD PLAN OUTPUT SCREEN

FIG.14

PET OUTPUT SCREEN (1)

| MENU |
|---|
| CLINICAL DATA INPUT |
| DRAINED-FLUID-VOLUME CURVE CREATION |
| D/P CURVE CREATION |
| ANALYSIS RESULTS |
| END |

PET Creatinine D/P ratio

PCREATININE DYNAMIC PARAMETER

MTAC = 12.35 mL/min   REFLECTION COEFFICIENT = 0.271 [−]

RESIDUAL RENAL FUNCTION = 0.101 ml/min   PRODUCTION RATE = 0.648 mg/min

CALCULATION RESULT
(MEDIUM-OSMOTIC-PRESSURE DIALYSIS SOLUTION · CREATININE)

RETENTION PERIOD = 240.0 min   CONCENTRATION IN DIALYSIS SOLUTION = 10.36 mg/dL

DRAINED FLUID VOLUME = 2350.0 mL   CONCENTRATION IN BODY FLUID = 14.00 mg/dL

AVERAGE DRAINED FLUID VOLUME = 2314.56 mL   D/P AT DRAINAGE = 0.74 [−]

[ Calculation ]  [ PET D/P ]  [ Back ]

[ help ]

MASS TRANSFER MECHANISM IN PERITONEAL DIALYSIS

PLANNING METHOD AND APPARATUS FOR PERITONEAL DIALYSIS AND HEMODIALYSIS HYBRID REMEDY

BACKGROUND OF THE INVENTION

This application is a divisional of application Ser. No. 10/555,701, filed Aug. 31, 2006 which is the National Stage of International Application No. PCT/JP2004/006863, filed May 14, 2004.

I. Technical Field

The present invention relates to a planning method and apparatus for peritoneal dialysis and hemodialysis hybrid remedy.

II. Description of Related Art

There are presently about 200,000 patients with chronic renal failure in Japan. Of them, 92% to 93% receive a treatment using hemodialysis while the remaining 7% to 8% being treated with peritoneal dialysis.

"Dialysis" here means a process of removing molecules from body fluid due to a concentration gradient by filtering it across a membrane, making use of different molecular weights. Thus, this process assists impaired renal function of the patients by transferring various substances which are accumulated in the body through metabolic activities—solutes (such as urea (U) as a uremic toxin and creatinine (Cr)), electrolytes ($Ca^{2+}$, $Cl^-$, $Na^+$, and $K^+$), excess water and the like—out of the body fluid into a dialysis solution, and by then discharging the dialysis solution from the body as drained fluid. Two distinguished modalities used for dialysis treatment are hemodialysis (HD) and peritoneal dialysis (PD). Hemodialysis involves filtration of blood using a dialysis solution while peritoneal dialysis is a procedure in which a dialysis solution is infused into the peritoneal cavity. Conventionally, either one of the dialysis procedures has been applied to the patients.

In recent years from 1990's onward, a hybrid remedy with peritoneal dialysis and hemodialysis (PD-HD) has gradually been applied to clinical practice in Japan, coupled with coverage for dialysis treatment by health insurance. In the hybrid remedy, PD is employed with the purpose of alleviating a burden on the patients and preferably making use of the residual renal function as much as possible while HD is concomitantly used as an auxiliary measure.

A PD system in which a condition of a patient's peritoneal function is simulated by a computer has recently been developed (see Japanese Laid-Open Patent Application Publication No. 2000-140100). This PD system enables testing aspects of peritoneal function, such as the rates of solute removal and transperitoneal water removal, by computing Pyle-Popovich's mathematical model—known as a macroscopic model of PD—from patient's data (the concentration of each solute, the volume of water removal and so on, included) obtained by using PET (Peritoneal Equilibration Test, 1987). Herewith, a PD schedule for a week, for instance, can be worked out.

However, the above PD system is specialized to plan a schedule for PD, and a problem remains that dialysis planning for a PD-HD hybrid remedy is difficult to establish. That is, although there are conventionally modality-specific parameters for PD and HD, respectively (clearance, the number of dialysis sessions, etc.), when it comes to dialysis planning for the hybrid remedy, a parameter shared between these two modalities is not yet known, and therefore creating the dialysis schedule is comparatively difficult. For this reason, the establishment of a planning method allowing to work out an accurate dialysis schedule for the hybrid remedy has been called for.

SUMMARY OF THE INVENTION

The present invention has been made in view of the above problem, and aims at offering a method and apparatus that exercise fair PD-HD hybrid-remedy planning by providing a prescription examination parameter shared between PD and HD.

In order to solve the above problem, the present invention uses an index that is shared by both peritoneal dialysis and hemodialysis and indicates the dialysis effect.

To be specific, the index for peritoneal dialysis and hemodialysis hybrid-remedy planning is $M/C(0)/V_B$, which is obtained by dividing a ratio $M/C(0)$—where M is the removal amount of a solute for a fixed time period, and $C(0)$ is the concentration of the solute in blood before the dialysis—by the body fluid volume of a patient, $V_B$.

In addition, the present invention uses a ratio $M/C(0)$—where M is the removal amount of a solute for a fixed time period, and $C(0)$ is the concentration of the solute in blood before the dialysis—as the index for the peritoneal dialysis and hemodialysis hybrid-remedy planning.

The effect of PD and HD is conventionally comprehended only by using modality-specific parameters for PD and HD, respectively. Planning of a PD-HD hybrid remedy is very difficult since no prescription examination parameter shared between PD and HD is known. However, the present invention uses the initial value of $M/C(0)$ or $M/C(0)/V_B$ as a parameter shared between PD and HD, and is thereby capable of representing the dialysis effect of PD and HD as an integrated sum and achieving concise and explicit PD-HD hybrid-remedy planning.

Accordingly, the present invention enables an examination of ideal PD-HD hybrid-remedy planning by (1) configuring some setting conditions so that $M/C(0)/V_B$—the initial value divided by the body fluid volume—meets the reference value, and (2) conducting a simulation in which the dialysis intensity and the number of dialysis sessions for both PD and HD are adjusted.

Although Kt/V is known as an index of peritoneal function, this index cannot be used for a simple comparison between PD and HD in the same unit. However, the use of $M/C(0)/V_B$ enables the PD-HD comparison in the same unit as Kt/V, which achieves a dialysis plan free from influence of variations in physical attributes of the patients.

Such dialysis planning is desirable because it can be exercised in the same time span used for conventional planning prescriptions (e.g. a prescription in which peritoneal function of a patient is estimated from the clinical data derived from PET to configure the concentrations of dialysis solutions and the number of exchanges and the like, and a prescription in which the peritoneal function is estimated from the blood sample data to configure hemodialysis).

In addition, the present invention is capable of exercising more precise and accurate PD-HD planning by, specifically speaking, determining $M/C(0)/V_B$—the initial value divided by the body fluid volume, rather than by referring to one of the drained-fluid-volume curve and the D/P curve.

In this case, at least one of the drained-fluid-volume curve and the D/P curve can be obtained from results of computation using Pyle-Popovich model.

BRIEF DESCRIPTION OF THE DRAWINGS

FIG. 4 shows an example of a time chart for data acquisition (a protocol for peritoneal function testing);

FIG. 5 shows input items of acquired data;

FIG. 6 is a clinical data input screen to be presented on a display;

FIG. 7 is a flow diagram of a PD-HD hybrid-remedy planning program of the present invention;

FIG. 8 shows a data analysis result screen for creating drained-fluid-volume curves, to be presented on the display;

FIG. 10 shows a data analysis result screen for creating a D/P curve, to be presented on the display;

FIG. 12 shows an input screen for PD-HD hybrid-remedy planning, to be presented on the display;

FIG. 13 shows an output screen for the PD-HD hybrid-remedy planning, to be presented on the display;

FIG. 14 shows a PET output screen to be presented on the display;

DETAILED DESCRIPTION OF THE INVENTION

1. First Embodiment

A PD-HD hybrid-remedy planning apparatus of the present invention computes Pyle-Popovich model, known as a macroscopic PD model, and uses the computation results. Here, this mathematical model is first described prior to a description of the apparatus.

1.1 Mathematical Model for PD

Figure 17:
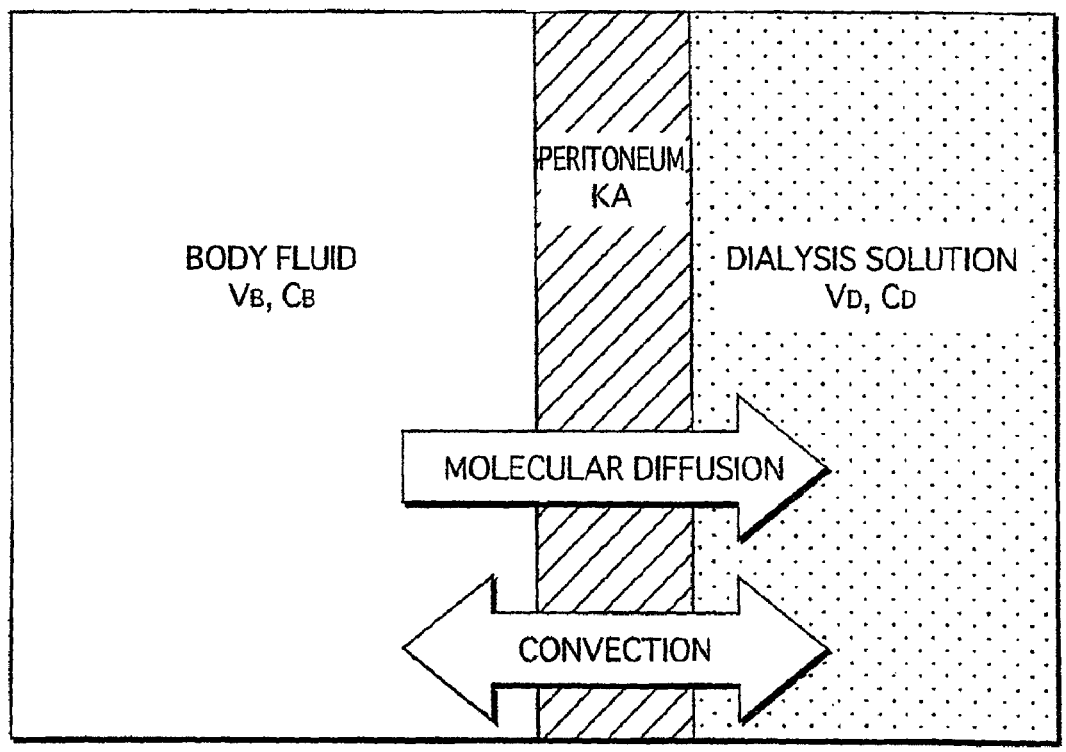
FIG. 17 is an explanatory diagram of Pyle-Popovich model.

FIG. 17 is a cross-sectional view of a peritoneum, concisely illustrating Pyle-Popovich model. The transfer of solutes from the body fluid to the dialysis solution via the peritoneum, which is assumed to be a homogeneous membrane, is represented by the sum of diffusion of solute molecules into the dialysis solution and convection (mass transfer due to the water movement—that is, convective transport, and a back flow due to absorption of the lymphatic system in the peritoneum), as shown by arrows in the figure. This mathematical model can be expressed as the following set of formulae (1-1) to (1-8) of the mathematical expression I.

[Mathematical Expression I]

$$G - \frac{dV_B C_B}{dt} - C_{LR} C_B = \frac{dV_D C_D}{dt} = \dot{m} \quad (1\text{-}1)$$

$$\dot{m} = KA(C_B - C_D) + Q_U(1-\sigma)\overline{C} \quad (1\text{-}2)$$

$$\overline{C} = C_B - f(C_B - C_D) \quad (1\text{-}3)$$

$$f = \frac{1}{\beta} - \frac{1}{\exp(\beta) - 1} \quad (1\text{-}4)$$

$$\beta = \frac{(1-\sigma)Q_U}{KA} \quad (1\text{-}5)$$

$$Q_U = a_1 \exp(a_2 t) + a_3 \quad (1\text{-}6)$$

$$V_D(t) = V_D(0) + \frac{a_1}{a_2}[\exp(a_2 t) - 1] + a_3 t \quad (1\text{-}7)$$

$$V_B + V_D = V_B(0) + V_D(0) \quad (1\text{-}8)$$

where t: time [min];
$C_{LR}$: residual renal function [mL/min];
$C_B$: concentration of a solute in blood [mg/mL];
$C_D$: concentration of a solute in the dialysis solution [mg/mL];
$V_B$: body fluid volume [mL];
$V_D$: drained fluid volume [mL];
β: Peclet number [–];
Qu: ultrafiltration rate (volume of ultrafiltration) [mL/min];
G: solute production rate [mg/min];
KA: overall mass transfer-area coefficient of peritoneum (MTAC) [mL/min];
σ: reflection coefficient [–];
$a_1$: empirical constant determining $Q_U$ [mL/min];
$a_2$: empirical constant determining $Q_U$ [1/min]; and
$a_3$: empirical constant determining $Q_U$ [mL/min].

Thus, Pyle-Popovich model is based on amass balance equation of individual solutes in the body fluid and those in the dialysis solution. In Pyle-Popovich model, items calculated for each patient are: an overall mass transfer-area coefficient KA (or MTAC) for each solute; a reflection coefficient σ; water removal parameters $a_1$, $a_2$ and $a_3$. Of them, the water removal parameters $a_1$, $a_2$ and $a_3$ are said to be particularly important for evaluating patient's capability of removing excess water from the body (referred to as "the water removal rate").

Empirical equations derived by Hume and Weyers can be used to calculate the body fluid volume ($V_B$) (Hume et al., 1971). According to sex, the empirical equations are expressed in terms of height [HT (cm)] and weight [WT (Kg)] of a patient as follows:

Male: $V_B(0)$=−14.249+0.19678HT+0.29571WT; and

Female: $V_B(0)$=−9.9260+0.17003HT+0.21371WT.

Although the water removal parameters $a_1$, $a_2$ and $a_3$ are determined from curve fitting of drained-fluid-volume curves, a value of each parameter can be estimated by using the modified Powell method which minimizes the error between clinical data and calculated values.

1.2 Configuration of PD-HD Hybrid-Remedy Planning Apparatus

Next is described the configuration of the PD-HD hybrid-remedy planning apparatus according to the first embodiment. The PD-HD hybrid-remedy planning apparatus can be established by implementing a program for executing a PD-HD hybrid-remedy planning method (a PD-HD hybrid-remedy planning program) on a general-purpose computer.

Figure 1:
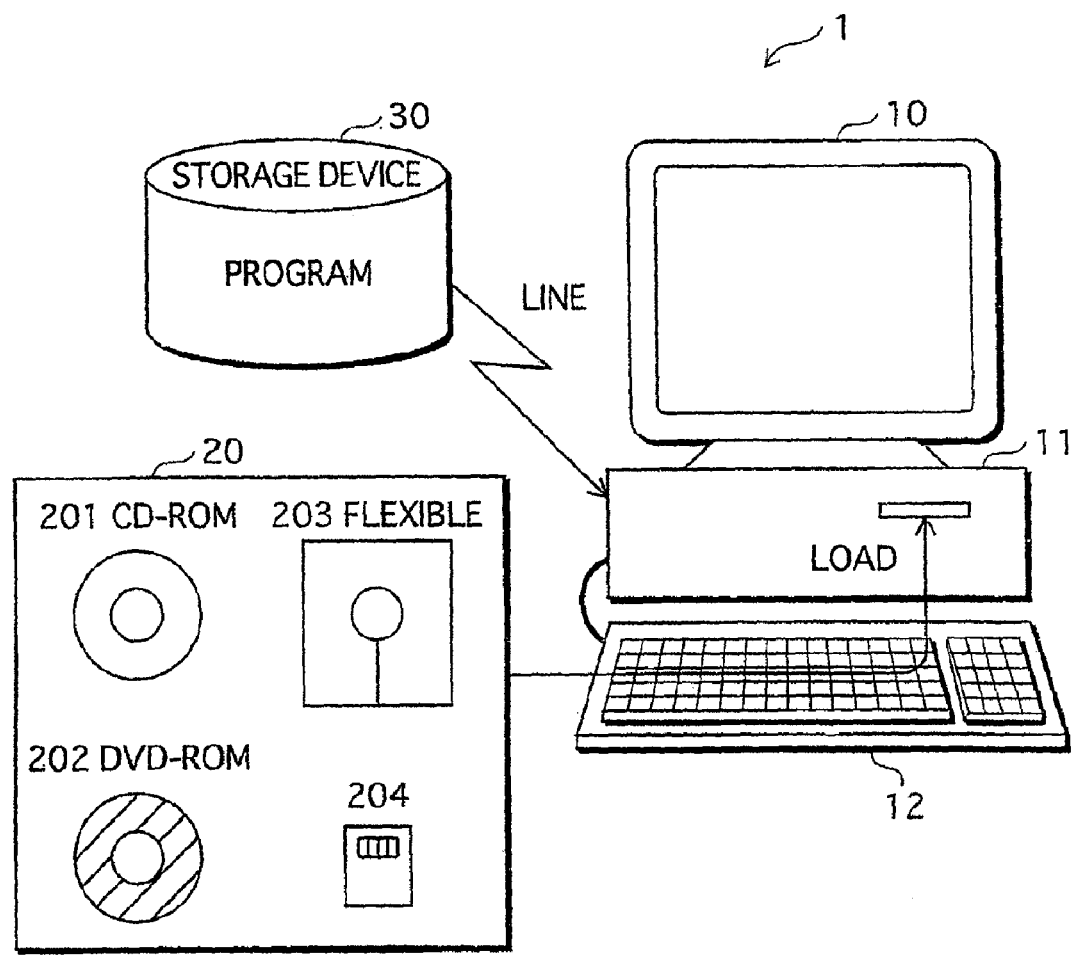
FIG. 1 is a schematic diagram of an applied example of the present invention—a PD-HD hybrid-remedy planning apparatus using a PC.

FIG. 1 shows a configuration example of the PD-HD hybrid-remedy planning apparatus.

The PD-HD hybrid-remedy planning apparatus is here shown as a personal computer (PC) 1 comprising: a main body 11; a keyboard 12 connected to the main body as input means; and a display 10.

The main body 11 has a basic configuration as a computer, having a general architecture which includes CPU, hard drives, memory and the like therein. The main body 11 is equipped with drive units for reading various transportable recording media 20 (a CD-ROM 201, a DVD-ROM 202, a flexible disc 203, and a memory card 204) placed from outside, and data or programs recorded on these recording media 20 are to be read into the CPU accordingly.

The keyboard 12 is connected to the main body 11. The keyboard 12 is an example of input means used by the operator to input data to the main body 11.

The display 10 is an example of data display (output means) connected to the main body 11. The display 10 shown here is formed by a CRT.

The PD-HD hybrid-remedy planning program may be, for example, read to the PC 1 from the various transportable recording media 20 (the CD-ROM 201, DVD-ROM 202, flexible disc 203, and memory card 204), or may be read to the PC 1 from a storage device 30, such as a different server or PC, via a communication line. It is desirable that the PD-HD hybrid-remedy planning program, once being read, be stored in a hard drive of the PC 1, along with patient's data.

The PD-HD hybrid-remedy planning apparatus uses a range of data obtained from a patient in a general clinical test (for example, Peritoneal Equilibration Test, or PET) as input data. The CPU of the PC 1 computes data obtained from PET and mathematical models of peritoneal function (such as Pyle-Popovich model). Then, based on data obtained as a result of the computation, such as the concentration of each solute, the water removal volume and the like, the CPU presents individual curves (drained-fluid-volume curves, a D/P curve, and time-course changes in blood concentration) on the display 10.

Here, the drained-fluid-volume curves are curves indicating ultrafiltration of dialysis solutions with low and medium osmotic pressures, while the D/P curve represents the ratio of the concentrations of a target solute in the dialysis solution and in the blood.

The contents presented on the display 10 assist examination of planning for a future PD-HD hybrid remedy. The present invention is herewith capable of accurately exercising PD-HD hybrid-remedy planning, which is conventionally difficult to achieve.

Note that the PD-HD hybrid-remedy planning apparatus has an advantage of making an effective use of conventional devices and data from the past, not requiring other special devices, calculation methods, new data which has previously never been used or the like, to fulfill the function.

1.3 Configuration of PD-HD Hybrid-Remedy Planning Program

Figure 2:
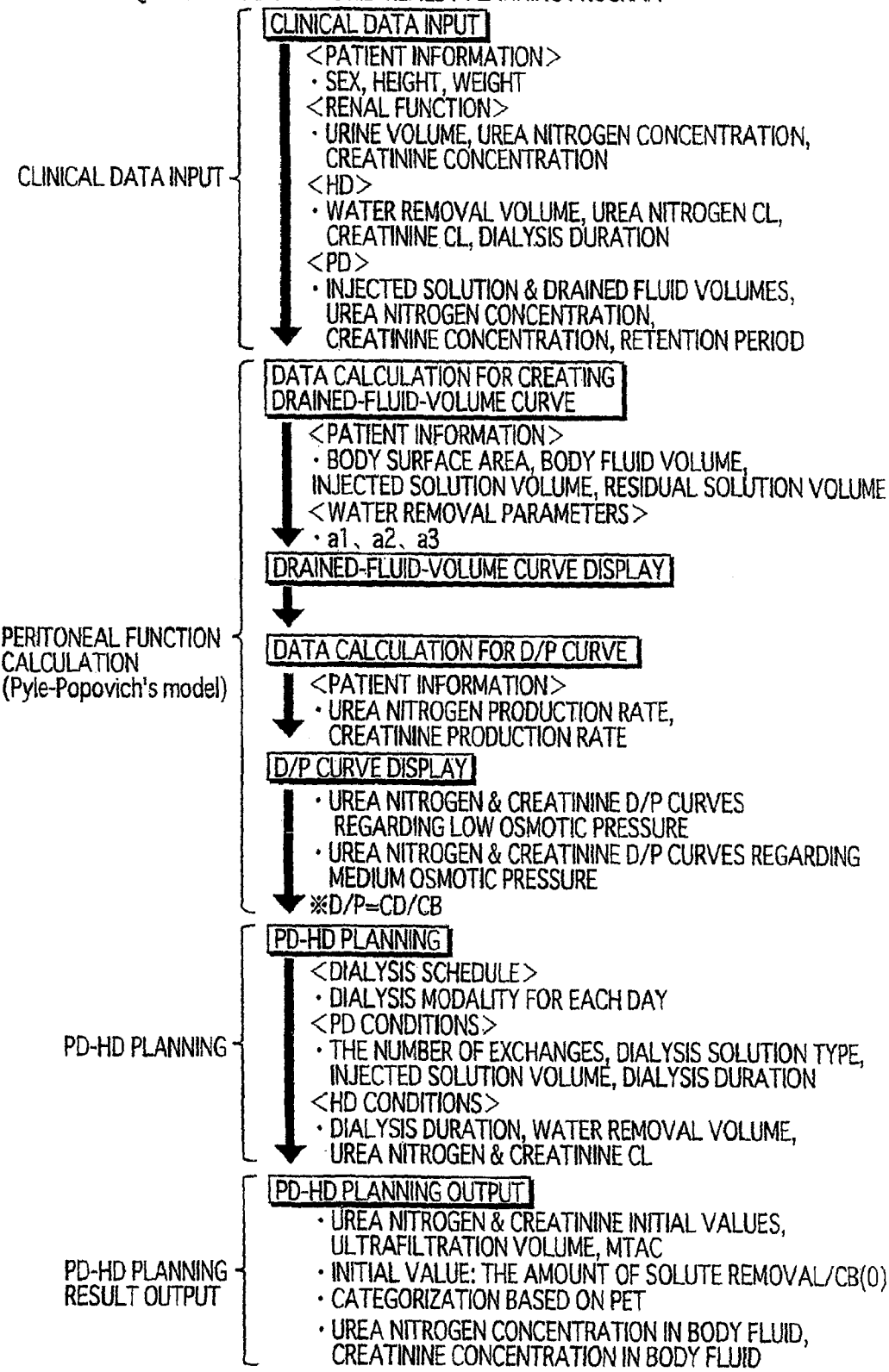
FIG. 2 shows an example of an operation sequence where the PD-HD hybrid-remedy planning apparatus is used.

The PD-HD hybrid-remedy planning program implemented on the PC 1 is configured to be generally executed in the following sequence. FIG. 2 shows a sequence of the program, from input of the data to display of calculation results.

Figure 9:
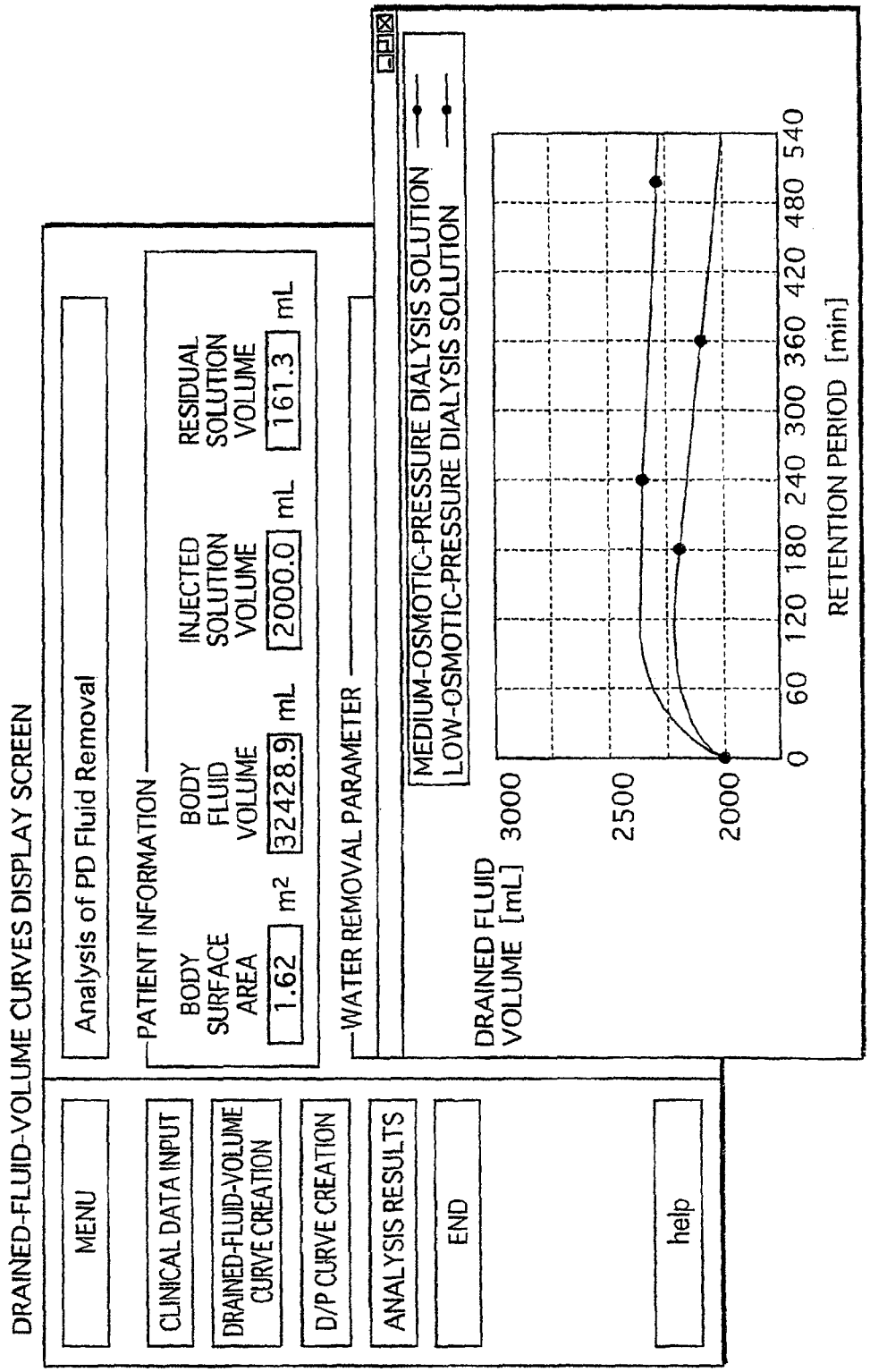
FIG. 9 shows the drained-fluid-volume curves to be presented on the display.

As shown in the figure, first, patient's clinical data required for PD and HD, respectively,—patient information, renal function, HD setting items and PD setting items—is input by the operator from a clinical data input screen (FIG. 6) presented on the display 10 of the PC 1. The program becomes executable after the data is input, and carries out various computations for PD and HD, including Pyle-Popovich model. Drained-fluid-volume curves, a D/P curve, and the concentration of a target solute in the blood are presented on the display 10 (FIGS. 9, 11 and 15, respectively), by using individual parameters obtained from the computations—such as the water removal parameters, body surface area, body fluid volume, injected solution volume, residual solution volume, urea nitrogen production rate, and creatinine production rate.

Based on each of these curves presented on the display 10, the operator sets a condition for each input item of the PD-HD hybrid remedy (PD-HD planning). To be specific, the operator specifies conditions on: a HD and PD dialysis schedule for a fixed period of time (here, on a weekly basis), in which scheduling for days when no dialysis treatment is performed is also incorporated; PD conditions (the osmotic pressure and volume of each dialysis solution, the retention periods, and the number of exchanges); HD conditions (the dialysis duration, water removal volume, urea nitrogen clearance, and creatinine clearance), and inputs these specified conditions from a PD-HD planning input screen (FIG. 12). The PC 1 calculates the initial value of the ratio M/C(0), using the amount of target-solute removal M and the concentration of the target solute in the blood before dialysis C(0) for the dialysis plan based on the input conditions. The ratio M/C(0) is divided by the body fluid volume $V_B$ to obtain $M/C(0)/V_B$, which is displayed as an integrated sum of divisional M/C(0)/$V_B$ planned to be achieved by HD, PD, and RRF (residual renal function), respectively (PD-HD planning output; FIG. 13).

The main feature of the present invention is to exercise the PD-HD hybrid-remedy planning by using an index shared by both PD and HD (i.e. $M/C(0)/V_B$, as an integrated sum of divisional $M/C(0)/V_B$ planned to be achieved individually by HD, PD, and RRF; or M/C(0)). Effectiveness and details of $M/C(0)/V_B$ and M/C(0) will be described when the operational sequence of the program is discussed.

As to the contents shown in FIG. 13, the operator checks whether or not the value of $M/C(0)/V_B$ reaches a predefined reference value. If the value is smaller than the reference value, the input conditions are adjusted in the PD-HD planning input screen (FIG. 12) so that the value becomes equal to or larger than the reference value. At this point, setting the proportion of PD in $M/C(0)/V_B$ as large as possible enables creating a schedule of the PD-HD hybrid remedy effectively utilizing residual renal function of the patient.

It is preferable that the reference value for weekly $M/C(0)/V_B$ be 2.0 or more. One reason for this is that DOQI guideline recommends setting Kt/V—a parameter equivalent to divisional $M/C(0)/V_B$ of PD—to 2.0 or more in order to maintain 5-year survival rates at 95% or more.

Furthermore, patients with loss of renal function in Japan generally receive HD treatment three times a week, and in the treatment, urea nitrogen $M/C(0)/V_B$ is prescribed to be 2.0 or more. In accordance with this, it is considered reasonable to set the reference value of weekly urea nitrogen $M/C(0)/V_B$ for the hybrid remedy to 2.0 or more. $M/C(0)_{un}/_c$, obtained by dividing urea nitrogen M/C(0) by creatinine M/C(0), represents the dialysis intensity, and the closer $M/C(0)_{un}/_c$ is to 1, the higher is the efficiency of uremic toxin removal.

1.4 Functional Blocks of PD-HD Hybrid-Remedy Planning Apparatus

Figure 3:
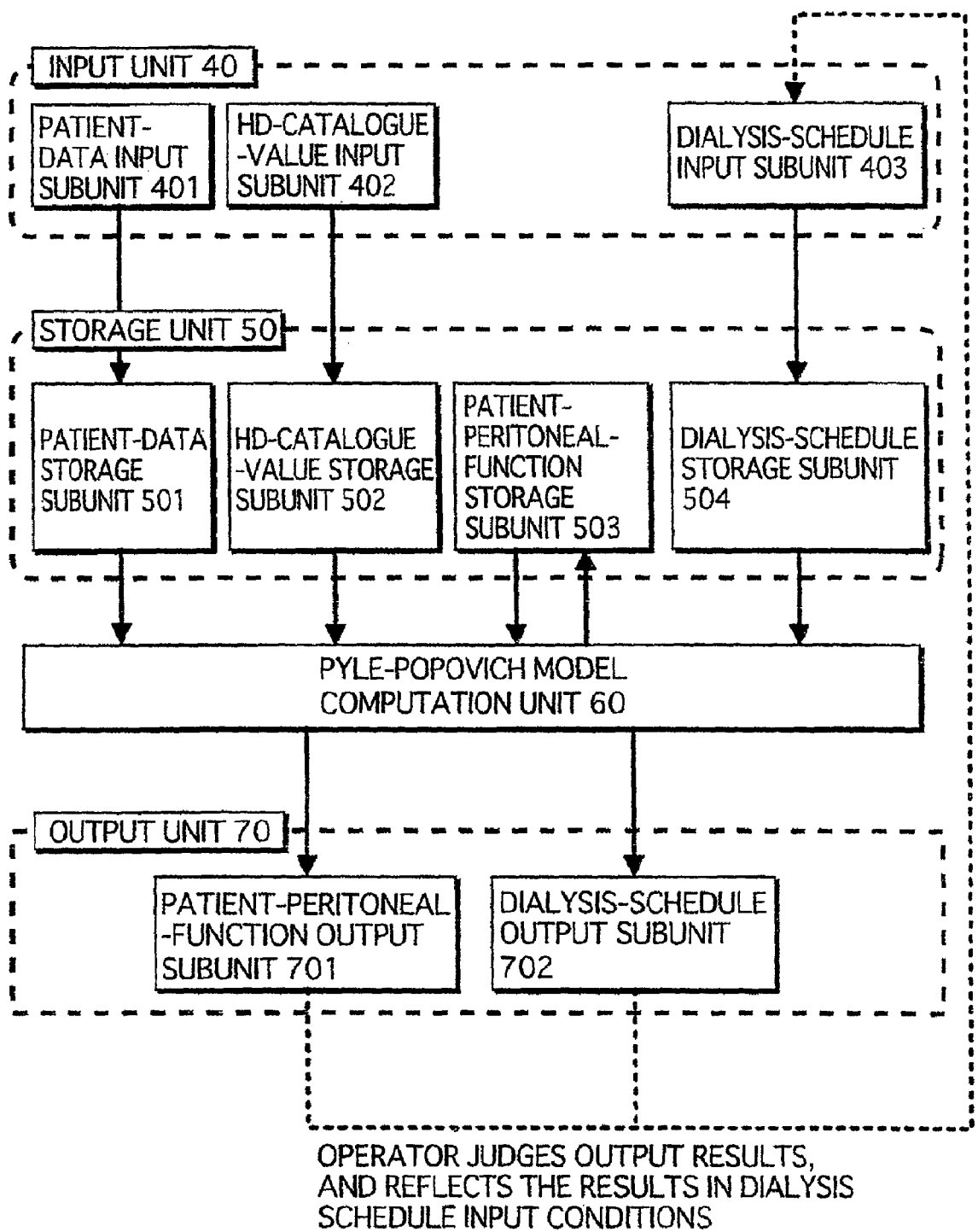
FIG. 3 is a functional block diagram of the PD-HD hybrid-remedy planning apparatus.

FIG. 3 illustrates functional blocks of the PD-HD hybrid-remedy planning apparatus.

As shown in the figure, the PD-HD hybrid-remedy planning apparatus having the above-mentioned PD-HD hybrid-remedy planning program stored in a hard drive thereof can be divided broadly into the following functional blocks: an input unit 40; a storage unit 50; a computation unit 60; and an output unit 70.

Of them, the input unit 40 comprises: a patient-data input subunit 401; a HD-catalogue-value input subunit 402; and a dialysis-schedule input subunit 403. On the other hand, the storage unit 50 includes: a patient-data storage subunit 501; a HD-catalogue-value storage subunit 502; a patient-peritoneal-function storage subunit 503; and a dialysis-schedule storage subunit 504, each of which is connected to the corresponding subunit inside the input unit 40.

The patient-data input subunit 401 receives patient's clinical data input by the operator via the keyboard 12, and stores the input clinical data into the patient-data storage subunit 501 of the storage unit 50.

The HD-catalogue-value input subunit 402, concretely speaking, receives set values of a dialyzer, and stores the set values into the HD-catalogue-value storage subunit 502 of the storage unit 50.

The dialysis-schedule input subunit 403 receives setting conditions for individual input items of the PD-HD hybrid-remedy planning, which is input by the operator via the keyboard 12, and stores these into the dialysis-schedule storage subunit 504 of the storage unit 50.

The storage unit 50 further includes the patient-peritoneal-function storage subunit 503, which is mutually connected to the computation unit 60.

The computation unit 60 accordingly receives data from the patient-data storage subunit 501, HD-catalogue-value storage subunit 502, patient-peritoneal-function storage subunit 503, and dialysis-schedule storage unit 504 of the storage unit 50, and performs a range of computations for PD and HD, including Pyle-Popovich model. When the computation unit 60 is in operation, computation required to establish a model (e.g. determination of reflection coefficients) is iterated, and therefore the computation unit 60 is configured to store a newly computed result into the patient-peritoneal-function storage subunit 503, overwriting a previously stored result, and then perform computation again.

The computation unit 60 is connected to the output unit 70, which comprises a patient-peritoneal-function output subunit 701 and a dialysis-schedule output subunit 702.

The patient-peritoneal-function output subunit 701 outputs data indicating peritoneal function of the patient (for example, the drained-fluid-volume curves and D/P curve) based on the computational result of Pyle-Popovich model obtained by the computation unit 60.

On the other hand, the dialysis-schedule output subunit 702 outputs a schedule of the PD-HD hybrid-remedy planning—a feature of the present invention—based on the computational result of Pyle-Popovich model obtained by the computation unit 60.

Note that the operator assesses the computational result output by the output unit 70, and inputs data again to the dialysis-schedule-input subunit 403 of the input unit 40, if necessary. Herewith, the computation is iterated, resulting in creating a more ideal dialysis schedule.

1.5 Practical Example

In order to make the apparatus operate, first, data acquired from a patient is required. A method for acquiring the data is described next, prior to an explanation of the apparatus operation.

1.5.1 Acquisition and Input of Clinical Data

Here are shown a procedure for the above-mentioned PD-HD hybrid-remedy planning of the present invention and an example of data acquisition steps. FIG. 4 shows the data acquisition steps (a protocol for peritoneal function testing). In the data acquisition steps, dialysis solution exchange, which starts in the evening of a previous day, is performed on a patient four times in total at intervals of retention periods of 6 hours, 3 hours, 8 hours, and 4 hours. Dialysis solutions used in the exchange procedure are ones with a low osmotic pressure (360 mOsm/kg-solvent) and with a medium osmotic pressure (400 mOsm/kg-solvent), and two sets of each are used in the stated order, as shown in the figure. Herewith, drained fluid samples D1 to D6 are collected (D1 to D3 are individually collected from the first three exchange sessions while D4 to D6 are collected from the last session), and drained fluid volumes (water removal volumes) VDL1, VDL2, VDM1 and VDM2 are individually measured. After the completion of dialysis, a blood sample (B1) for HD is collected. During a series of testing shown in FIG. 4 being conducted, a urine collection (U1) is performed while a urine volume ($V_U$) being measured.

In the practical example here, dialysis solution is exchanged twice or more with respect to each osmotic pressure; however, the present invention can be carried out if at least two sets of drained fluid data for a single level of osmotic pressure are obtained, as described above. While conventional peritoneal function testing requires 36 hours or more in total since at least three sets of drained fluid data for each osmotic pressure are collected, the present invention requires a smaller number of drained fluid data sets as compared to the conventional testing, and the protocol for peritoneal function testing can be completed in about 24 hours.

Therefore, the present invention allows a comparatively quick examination of PD-HD hybrid-remedy planning. Note that FIG. 4 illustrates an example in which two different retention periods are established for each osmotic pressure in order to solve Pyle-Popovich formulae.

Items of patient's data herewith obtained are sorted out as input data, as shown in a chart of FIG. 5. Namely, in the above-mentioned data acquisition steps, obtained as clinical data for PD are: the solute concentrations of urea and creatinine; the drained fluid volumes (VDL1, VDL2, VDM1 and VDM2); and the retention periods for the samples D1 to D6. The samples D4 to D6 are used for PET. On the other hand, the blood sample is examined to determine the solute concentrations of urea and creatinine. Acquired from the urine sample U1 are: the urea concentration; the creatinine concentration; the urine volume $V_U$ and the like.

Based on such patient's data in FIG. 5, the operator inputs information of predefined items from the clinical data input screen (FIG. 6) presented on the display 10. FIGS. 6 and 8 to 16, to be hereinafter described, show screen examples of when data obtained from a given patient, Patient A, is used as input data.

Items to be input comprises as follows: (1) patient information including sex, height and weight; (2) information on renal function including the urea nitrogen and creatinine concentrations derived from the blood sample, and the urine volume; (3) information on HD conditions including the urea nitrogen clearance, creatinine clearance, dialysis duration, and water removal volume (note however that, for these HD items, catalogue values of the dialyzer can be input for the initial time, and measured values are used from the second time onward to raise accuracy); and (4) information on PD conditions including the injected solution volume, and the urea nitrogen concentration, creatinine concentration, drained fluid volume, and retention period with respect to each of D1 to D6 and B1.

Note that, for the numerical values of the dialyzer above, the present embodiment may always use fixed values (for example, the catalogue values, or numerical values predicted based on an empirical rule and/or patient's previous data), or may instead use some numerical values prepared in advance. Herewith, the PD-HD hybrid-remedy planning can be carried out only with clinical data on the peritoneum (data of the peritoneal function testing), not requiring a blood test to be conducted, which therefore leads to a simpler exercise of PD-HD hybrid-remedy planning with a smaller amount of data.

In addition, in the present embodiment, graph display is made possible by using numerical values obtained from at least two sets of the clinical data.

1.5.2 Operation of PD-HD Hybrid-Remedy Planning Apparatus

Once the data input to the PD-HD hybrid-remedy planning apparatus is completed, the program of the PD-HD hybrid-remedy planning apparatus (the PD-HD hybrid-remedy planning program) can be executed.

FIG. 7 is a flow diagram showing exemplified steps of the PD-HD hybrid-remedy planning program.

As shown in the figure, after the program is launched on the PC 1, the PC 1 first judges whether or not data required to compute a Pyle-Popovich model has been input according to the program (Step S101).

If a sufficient amount of data has been input, the PC 1 computes Pyle-Popovich model of the above mathematical expression I, based on the input patient's clinical data (Step S102). This computation determines the overall mass transfer-area coefficients for urea nitrogen ($MTAC_{un}$) as well as for creatinine ($MTAC_c$), the water removal parameters $a_1$, $a_2$ and $a_3$, and so on. Note that how to compute the simultaneous equations of Pyle-Popovich model is specifically described in Japanese Laid-Open Patent Application Publication No. 2000-140100.

The PC 1, in addition, calculates the body surface area (BSA) of a patient in $m^2$, by assigning the patient's height and weight into the mathematical expression II (BSA calculation; Gehan, 1970).

$$BSA=0.0235 \cdot (100 \cdot L) \exp(0.4226) \cdot W \exp(0.51456) \qquad \text{[Mathematical Expression II]}$$

where, L is height [m]; and

W is weight [kg].

In the case of Patient A with a height of 159.5 cm and a weight of 58.1 kg, BSA of Patient A is 1.62 $m^2$ according to the mathematical expression II. After the BSA calculation, the PC 1 presents, on the display 10, a data analysis result screen for creating the drained-fluid-volume curves (FIG. 8), according to the program. Presented in the figure are: patient information including the body surface area, body fluid volume, injected solution volume, and residual solution volume; and the water removal parameters $a_1$, $a_2$ and $a_3$ of the dialysis solutions with a low and a medium osmotic pressure obtained by computing approximation solutions based on Pyle-Popovich model and the modified Powell method. The operator checks the information, and directs the PC 1 to carry out calculation for drained-fluid-volume curves, which are subsequently presented on the display 10 (FIG. 9) (Step S103).

Note that, at this point, the first embodiment is capable of displaying results obtained from PET (data on a creatinine D/P ratio of FIG. 14; and PET curves of FIG. 16) instead by modifying the program's set items.

Subsequently, the PC 1 causes the display 10 to present, data analysis result screen for creating the D/P curve (FIG. 10), based on the clinical data input from the data input screen of FIG. 6. Here presented are such as: a parameter estimation method; patient information including the solute production rates with respect to urea nitrogen and creatinine; and dynamic parameters including the overall mass transfer-area coefficients (KA=MTAC) of individual solutes and reflection coefficients (σ). The operator checks the information, and directs the PC 1 to carry out calculation for the D/P curve, which is subsequently presented on the display 10 (FIG. 11) (Step S103). Examination of the D/P curve allows to see whether the clinical data and the calculation results match each other. In addition, by comparing the drained-fluid-volume curves against the D/P curve, it is possible to examine a schedule for dialysis solution exchanges where the amount of solute removal and water removal volume are taken into account.

Here, by modifying screen settings of the display 10, only either the drained-fluid-volume curves or the D/P curve can be presented, or alternatively the both can be presented in the same screen. In this case, the calculation of drained-fluid-volume curves is performed first, which is then followed by the calculation of D/P curve.

Figure 11:
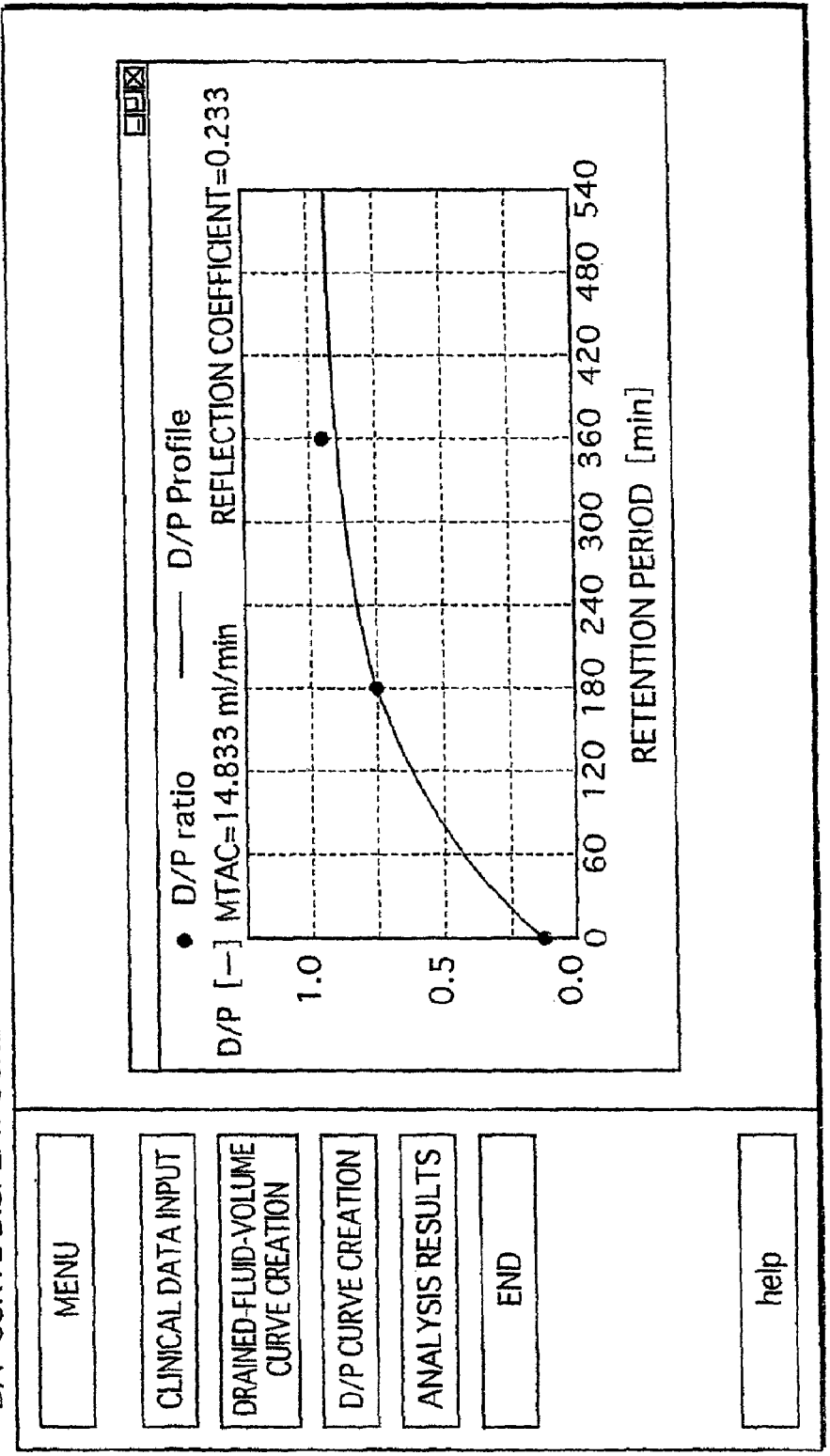
FIG. 11 shows the D/P curve to be presented on the display.

Here, the operator checks the parameters for patient's peritoneal function (MTAC, σ, $a_1$, $a_2$, and $a_3$) in reference to individual curves of FIGS. 10 and 11, to then exercise PD-HD hybrid-remedy planning.

To be concrete, the operator configures predefined setting items from a daily prescription input screen for PD-HD hybrid-remedy planning, shown in FIG. 12. Specific setting items are: PD and HD for a fixed period of time (here, a week—known as a unit of time period employed for a general dialysis schedule; allocation of days on which no dialysis treatment is performed; PD conditions (the osmotic pressure and volume of each dialysis solution, the number of exchanges, and the retention periods); and HD conditions (the dialysis duration, water removal volume, urea nitrogen clearance, and creatinine clearance). Once data input is made for these setting items for PD-HD hybrid-remedy planning, the PC 1, according to the program, judges whether or not the data has been properly input (Step S104) and then calculates the remedy efficiency based on the schedule (Step S105).

Here, the PC 1 calculates, with respect to each PD and HD, the amount of each solute removal M (mg/week), the concentration of each solute (urea and creatinine) in the blood C(0) (mg/mL), and the initial value of the ratio M/C(0) (L/week) for a fixed period of time—a week, in the first embodiment. The PC 1 further calculates M/C(0) (L/week), which is an integrated sum of divisional M/C(0) planned to be achieved by PD and HD, respectively. This calculation process is a feature of the present embodiment. To be more specific, M/C(0) is calculated with respect to each PD and HD for every dialysis treatment, and a total M/C(0) (L/week) is determined by adding all M/C(0) for seven days. The total M/C(0) (L/week) is then divided by the body fluid volume $V_B$ of the patient to obtain $M/C(0)/V_B$.

The PC 1 directs the display 10 to present thereon the result, and thereby a PD-HD hybrid-remedy planning screen (FIG. 13) is displayed (Step S106).

Note that the "fixed period of time" cited here is a unit of time period that represents a specific time segment for the dialysis planning. Therefore, as a matter of course, it can take a time frame other than a week. The total M/C(0) (L/week) shown in FIG. 13 is calculated by further adding divisional M/C(0) of RRF to the PD-HD integrated sum of M/C(0)—namely, the total M/C(0) is composed of divisional M/C(0) of PD, HD, and RRF, respectively; however, FIG. 13 shows only a fractional portion of RRF since Patient A has a very small RRF value.

$M/C(0)/V_B$ has for the first time been discovered, by the present inventors, as a parameter index (criterion) shared between PD and HD in a PD-HD hybrid remedy.

That is, the dialysis effect using PD and HD is conventionally determined only by parameters specific to the respective dialysis modalities. Since there is no common parameter which can be used as an index to examine prescription for a PD-HD hybrid remedy, PD-HD hybrid-remedy planning has been very difficult to exercise. However, the first embodiment is capable of using $M/C(0)/V_B$—representing the integrated sum of divisional $M/C(0)/V_B$ of HD and PD—as a concise and accurate index for PD-HD hybrid-remedy planning (i.e. an indicator of the dialysis effect of the PD-HD hybrid remedy). The value of $M/C(0)/V_B$ can be controlled as many times as desired by modifying some of the previously input conditions from the input screen shown in FIG. 12 and then conducting a simulation while adjusting the dialysis intensity and the number of dialysis sessions for both HD and PD plans. This allows to consider the best-suited PD-HD hybrid-remedy planning in which QOL (quality of life) of the patient is taken into full account.

In addition, the use of $M/C(0)/V_B$ enables a comparison against Kt/V—a conventionally well known parameter—in the same dimension, which in turn allows a dialysis plan to be examined without influence of variations in physical attributes of the patients (individual difference in the body fluid volume). It is preferable that the reference value for weekly $M/C(0)/V_B$ be 2.0 or more. One reason for this is that DOQI guideline recommends to set Kt/V—a parameter equivalent to divisional $M/C(0)/V_B$ of PD—to 2.0 or more in order to maintain 5-year survival rates at 95% or more. Furthermore, patients with loss of renal function in Japan generally receive HD treatment three times a week, and in the treatment, urea nitrogen $M/C(0)/V_B$ is prescribed to be 2.0 or more. Thus, the first embodiment has successfully simplified PD-HD hybrid-remedy planning, which is conventionally very difficult to achieve, by using the PD-HD shared parameter of the same dimension.

To be specific, the first embodiment is capable of judging the adequacy of currently examined PD-HD hybrid-remedy planning based on whether or not weekly $M/C(0)/V_B$ is 2.0 or more. It is preferable that the reference value for weekly $M/C(0)/V_B$ be 2.0 or more. One reason for this is that DOQI guideline recommends to set Kt/V—a parameter equivalent to divisional $M/C(0)/V_B$ of PD—to 2.0 or more in order to maintain 5-year survival rates at 95% or more. Furthermore, patients with loss of renal function in Japan generally receive HD treatment three times a week, in the treatment, urea nitrogen $M/C(0)/V_B$ is prescribed to be 2.0 or more. As a matter of course, the reference value, 2.0, can be changed adequately, for example, when the parameter is applied to non-Japanese patients.

In short, the operator accordingly configures, from the input screen shown in FIG. 12, the setting conditions for: PD and HD plans; a schedule for days when no dialysis treatment is performed; and the number of dialysis sessions, and repeats the setting procedure so that the values of weekly urea and creatinine $M/C(0)/V_B$ presented as in FIG. 13 individually become 2.0 or more. At this point, it should be assured that PD accounts for as large a proportion of the dialysis schedule as possible in order to utilize residual renal function of the patient. Since using a relatively concise index of weekly $M/C(0)/V_B$ (L/week) being simply set to be 2.0 or more, the first embodiment is capable of exercising PD-HD hybrid-remedy planning in a dramatically simple and accurate manner, as compared to conventional complicated dialysis planning compositely taking into account different parameters, each of which is specific to either PD or HD.

As an example of the PD-HD hybrid-remedy planning of the first embodiment, the case shown in FIGS. 12 and 13 is described next.

As to Patient A, the operator sets a schedule of one week in the input screen of FIG. 12 as follows: PD on Monday to Friday; HD on Saturday; and no dialysis treatment on Sunday. The PD plan is set so that a dialysis solution of 2000 mL with an osmotic pressure of 360 (mOsm/kg-solvent) is to be exchanged four times a day. With respect to the HD plan, adequate settings—the drive condition of the dialyzer and the like included—are configured (the explanation is here omitted for simplification).

Assume that, when such settings have been made, the value obtained for urea nitrogen $M/C(0)/V_B$ is 1.89 while the value of creatinine $M/C(0)/V_B$ becomes 1.52, both falling short of the reference value of 2.0, as shown in the output screen of FIG. 13. In this case, the operator judges that the current PD-HD hybrid-remedy schedule is inadequate (i.e. the dialysis treatment is insufficient), and returns to the input screen of FIG. 12 once again to change the setting conditions. Because the number of setting items to be changed is limited, this operation is simple. In the case here, setting conditions to be changed are, for example: the number of daily dialysis sessions; the volume of dialysis solution; and the number of weekly HD treatments. An increase in any of these setting items results in enhancing the dialysis intensity. The operator changes conditions for the respective dialysis plans in the input screen of FIG. 12, taking into account the patient's daily rhythm, the physical condition and the like, so that the ultimate weekly $M/C(0)/V_B$ shown in FIG. 13 satisfies the target value, 2.0 or more.

Note that, in the case when the number of weekly HD treatments needs to be three times or more in order to achieve a weekly $M/C(0)/V_B$ of 2.0 or more, it is desirable that Patient A be treated by HD only, instead of a PD-HD hybrid remedy. This is because a general HD-only remedy conducts HD treatments three times a week, which indicates that the patient is substantially impossible to be treated by PD. While showing the effect that would be achieved by the PD-HD hybrid-remedy planning, the first embodiment can thus be used as an indicator for judging what kind of dialysis modality is desired to be applied to each patient.

Although it has been described that weekly $M/C(0)/V_B$ is preferable to be 2.0 or more, it is not recommended to enhance the dialysis intensity so much that weekly $M/C(0)/V_B$ exceeds far beyond 2.0, which results in imposing a burden on the patient. In order to reduce the patient's burden, or to promote a gradual transition from PD to HD in view of the patient's time-course change in dialysis capability (the mechanism of deterioration in peritoneal function), it is desirable to set weekly $M/C(0)/V_B$ to be approximately 2.0, as has been described above.

Figure 15:
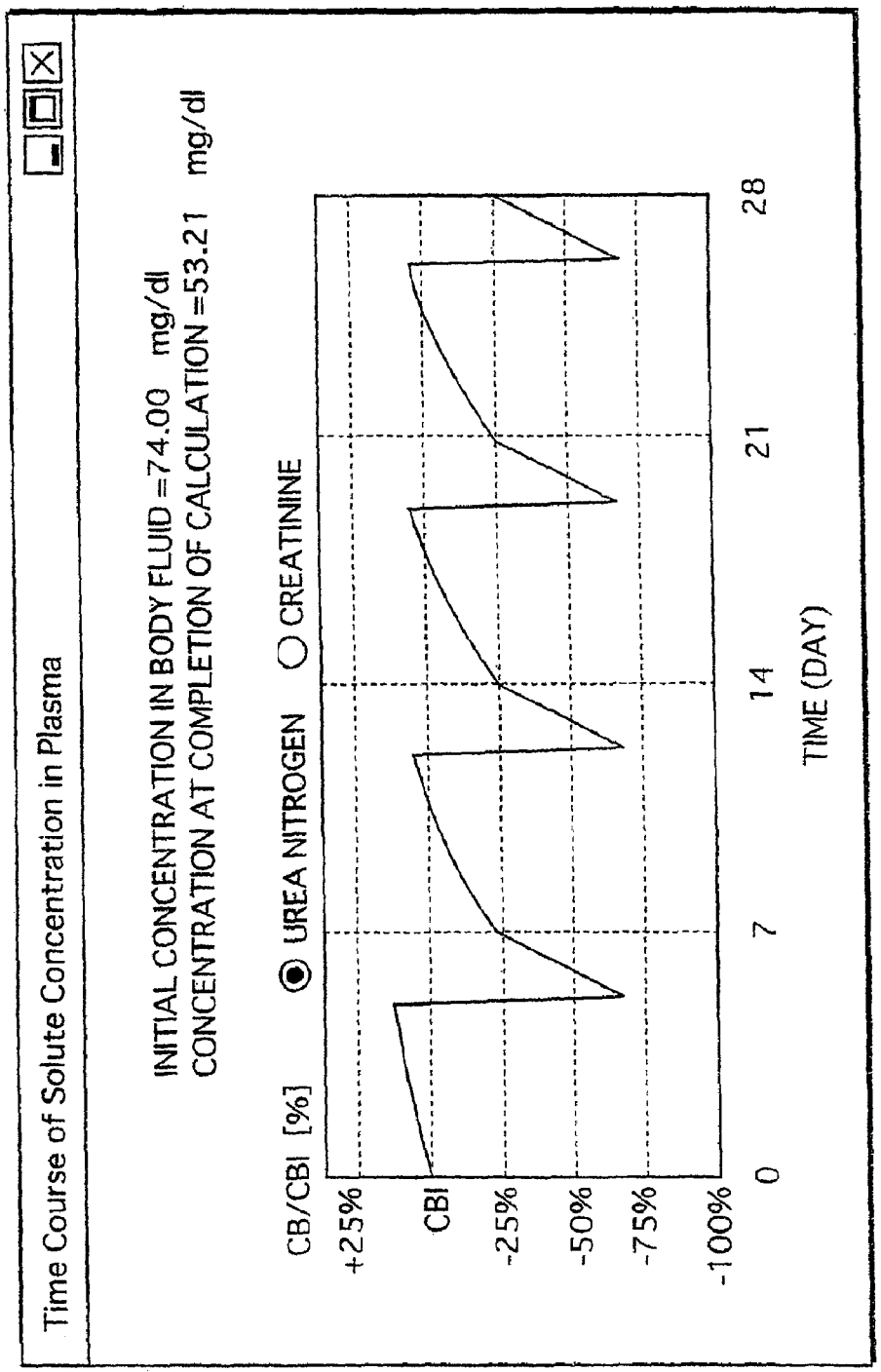
FIG. 15 is a graph of changes in blood concentration, to be presented on the display.
Figure 16:
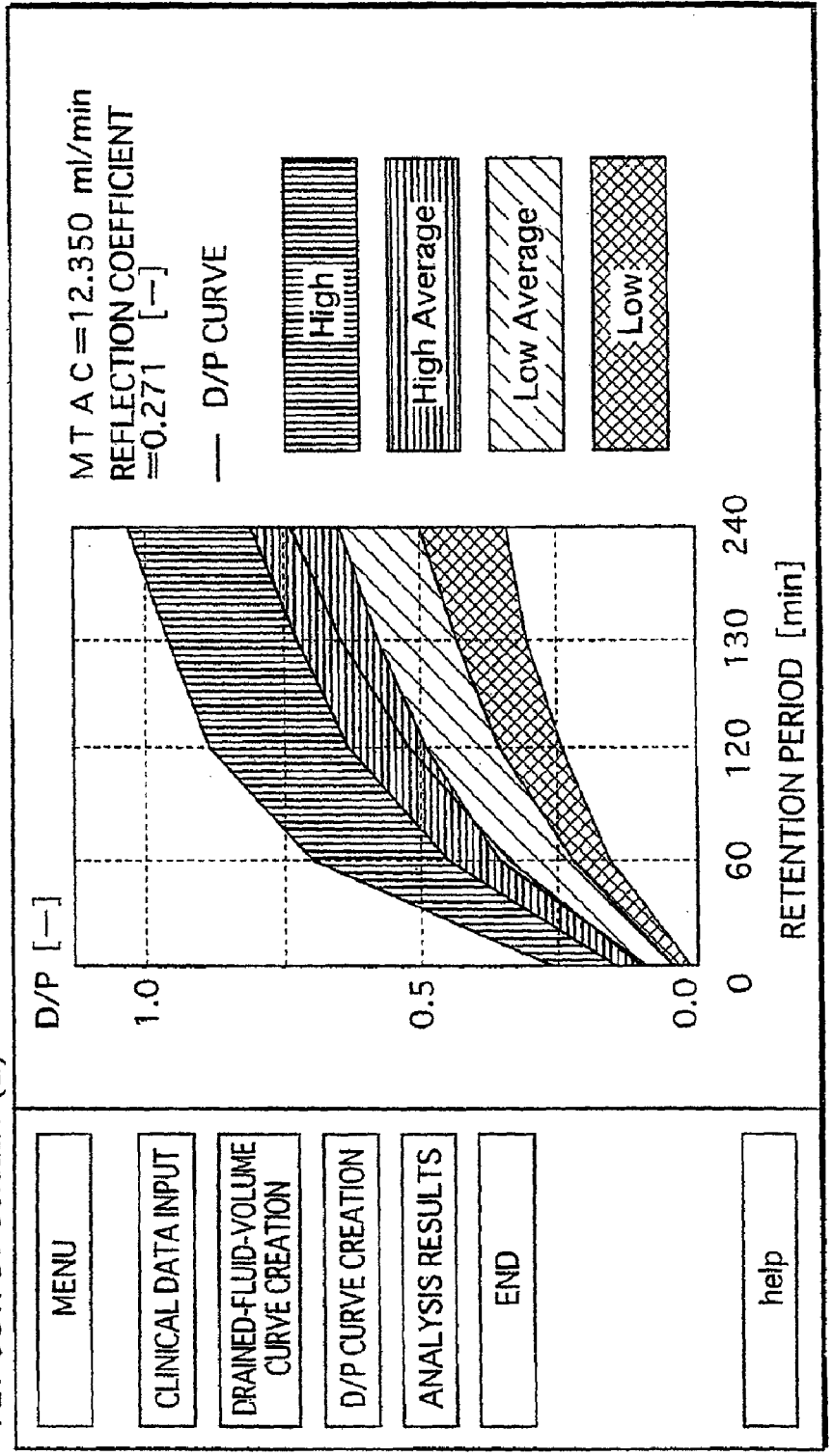
FIG. 16 shows another PET output screen to be displayed on the display.

The effect of the dialysis planning configured in the above-described manner can be learned, for example, from an output screen of the blood concentration changes in FIG. 15. Here are shown changes of the urea nitrogen concentration in the blood during a dialysis remedy of 28 days in total (i.e. four weeks). If the dialysis plan is adequate, peaks of the curve in the figure would take low values. Herewith, the effect of the configured dialysis planning can be determined. The data on the blood concentration changes can be obtained by calculating peritoneal function based on the PD conditions of FIG. 6, and running a simulation by applying the calculated peritoneal function to the dialysis schedule.

In addition, the first embodiment is able to use the initial value of the ratio $M/C(0)$ itself as an index of the PD-HD hybrid-remedy planning, as shown in FIG. 13. In this case also, the ratio $M/C(0)$ can be calculated as an integrated sum of divisional $M/C(0)$ of PD and HD, achieving nearly the same effect as when $M/C(0)/V_B$ is used. Thus, the first embodiment has successfully simplified PD-HD hybrid-remedy planning, which is conventionally very difficult to achieve, by using the PD-HD shared parameter of the same dimension. Note however that, when M/C(0) is used for the dialysis planning, physical attributes of each patient have to be taken into account.

In the example of FIG. 13, data regarding the water removal volume represented by ultrafiltration and the comparison between the overall mass transfer-area coefficient KA (MTAC) and M/C(0) is displayed together with M/C(0) and M/C(0)/$V_B$, which allows an examination of peritoneal function obtained by Pyle-Popovich model; however displaying such data is not indispensable. In this regard, however, the PD-HD hybrid-remedy planning is preferably configured in a manner that the contribution of PD and RRF (residual renal function) accounts for as large a proportion of the total water removal volume due to ultrafiltration—achieved by PD, HD, and RRF all together—as possible because this enables utilizing patient's residual physical function and reducing the treatment burden on the patient.

After displaying the output screen of FIG. 13 once, the PC 1 seeks an operator's direction concerning whether or not to complete the processing (Step S 107). At this point, if the operator desires to change the setting conditions for the PD-HD hybrid-remedy planning, the PC 1 returns to Step S104. When the setting conditions are ultimately determined, the PC 1 completes the program processing.

2. Additional Particulars

The first embodiment above describes an example in which the display 10 functioning as display means presents and outputs M/C(0) and M/C(0)/$V_B$; however, the present invention is not confined to this, and such data may be output by audio using speakers.

In addition, the above-mentioned example uses drained-fluid-volume curves and a D/P curve in order to determine M/C(0) and M/C(0)/$V_B$; however, these curves are not indispensable for the present invention, and other clinical data obtained from a patient (for example, data derived from PET only) may be used instead. Note that, when dialysis planning like the first embodiment is exercised, there is sufficient possibility that the retention periods for PD, for example, are set to time periods that were not used in the clinical test. With a retention period not found in the clinical test, the amount of target-solute removal M can only be found by estimation; a dynamic estimation model, such as Pyle-Popovich model, is largely effective for the estimation procedure.

In the above example, the formulae of Pyle-Popovich model are computed to derive the drained-fluid-volume curves; however, a mathematical model other than Pyle-Popovich model may be used instead.

INDUSTRIAL APPLICABILITY

The present invention is applicable to the examination of peritoneal dialysis and hemodialysis hybrid remedy in dialysis treatment.

The invention claimed is:

1. A peritoneal dialysis and hemodialysis hybrid-remedy planning apparatus comprising:
a storage unit programmed to obtain data from a dialysis patient;
a computation unit configured to perform a computation using the data obtained from the dialysis patient; and
an output unit configured to output the results of the computation, wherein
the computation unit is configured to perform the computation to obtain an index that is shared by both peritoneal dialysis and hemodialysis and indicates an effect of dialysis, and
the output unit is configured to output the index to be used for peritoneal dialysis and hemodialysis hybrid-remedy planning,
wherein the computation unit is configured to calculate a ratio M/C(0), where M is a removal amount of a solute for a fixed time period, and C(0) is a concentration of the solute in blood before the dialysis, and the output unit outputs the ratio M/C(0) as the index,
wherein the output unit is further configured to output at least one of a drained-fluid-volume curve and a D/P curve,
wherein the computation unit is configured to obtain the at least one of the drained-fluid-curve and the D/P curve from results of computation using a Pyle-Popovich model and using a modified Powell method, and
wherein M is obtained by a product of waste concentration in a drained fluid and a drained fluid volume as a value used for peritoneal dialysis, and by a product of clearance of a dialyzer and dialysis duration as a value used for hemodialysis, both the value used for peritoneal dialysis and the value used for hemodialysis being measured in the same units so as to achieve an integrated sum of values of M/C(0) planned to be achieved by peritoneal dialysis and hemodialysis for a fixed period of time.

2. The peritoneal dialysis and hemodialysis hybrid-remedy planning apparatus of claim 1, wherein the computation unit calculates M/C(0)$V_B$, which is obtained by dividing the ratio M/C(0) by a dialysis patient's body fluid volume, $V_B$, and
the output unit outputs M/C(0) $V_B$ as the index.

3. The peritoneal dialysis and hemodialysis hybrid-remedy planning apparatus of claim 1, wherein
the fixed time period is one week, and
the computation unit computes a schedule of the dialysis for the one week and the output unit outputs the schedule.

4. The peritoneal dialysis and hemodialysis hybrid-remedy planning apparatus of claim 1, wherein
M and C(0) are determined by a peritoneal function test.

5. The peritoneal dialysis and hemodialysis hybrid-remedy planning apparatus of claim 4, wherein
the peritoneal function test uses dialysis solutions with a plurality of levels of osmotic pressures and collects two sets of drained fluid data with respect to each of the plurality of levels of osmotic pressures, and
the computation unit determines M and C(0) based on the drained fluid data.

6. A computer-readable recording medium having recorded thereon a peritoneal dialysis and hemodialysis hybrid-remedy planning program, which uses a peritoneal dialysis and hemodialysis hybrid-remedy planning apparatus having a computation unit and an output unit, the computation unit performing a computation using data obtained from a dialysis patient and outputting results of the computation to the output unit, the peritoneal dialysis and hemodialysis hybrid-remedy planning program causing the computation unit to perform the steps comprising:
acquiring a removal amount of a solute for a fixed time period, M;
acquiring a concentration of the solute in blood before dialysis, C(0);
calculating a ratio M/C(0) using M and C(0);
calculating M/C(0) $V_B$ by dividing the ratio M/C(0) by a patient's body fluid volume, $V_B$, M being a removal amount of a solute for a fixed time period, and C(0) is a concentration of the solute in blood before the dialysis, calculating the ratio M/C(0) as an index and at least one of a drained-fluid-volume curve and a DP curve using a Pyle-Popovich model and using a modified Powell method; and wherein M is obtained by a product of waste concentration in a drained fluid and a drained fluid volume as a value used for peritoneal dialysis, and by a product of clearance of a dialyzer and dialysis duration as a value used for hemodialysis, both the value used for peritoneal dialysis and the value used for hemodialysis being measured in the same units so as to achieve an integrated sum of values of M/C(0) planned to be achieved by peritoneal dialysis and hemodialysis for a fixed period of time.

7. The computer-readable recording medium of claim 6, wherein the fixed time period is one week, and the peritoneal dialysis and hemodialysis hybrid-remedy planning program causes the computation unit to, in calculating one of a ratio M/C(0) and M/C(0) $V_B$, calculate with respect to a schedule of the dialysis for the one week.

8. A computer-readable recording medium having recorded thereon a peritoneal dialysis and hemodialysis hybrid-remedy planning program which uses a peritoneal dialysis and hemodialysis hybrid-remedy planning apparatus having a computation unit and an output unit, the computation unit performing a computation using data obtained from a dialysis patient and outputting results of the computation to the output unit, the peritoneal dialysis and hemodialysis hybrid-remedy planning program causing the computation unit to perform the steps comprising:

acquiring a removal amount of a solute for a fixed time period, M;

acquiring a concentration of the solute in blood before dialysis, C(0);

calculating a ratio M/C(0) using M and C(0), M being a removal amount of a solute for a fixed time period, and C(0) is a concentration of the solute in blood before the dialysis, calculating the ratio M/C(0) as an index and at least one of a drained-fluid-volume curve and a DP curve using a Pyle-Popovich model and using a modified Powell method, and wherein M is obtained by a product of waste concentration in a drained fluid and a drained fluid volume as a value used for peritoneal dialysis, and by a product of clearance of a dialyzer and dialysis duration as a value used for hemodialysis, both the value used for peritoneal dialysis and the value used for hemodialysis being measured in the same units so as to achieve an integrated sum of values of M/C(0) planned to be achieved by peritoneal dialysis and hemodialysis for a fixed period of time.

9. The computer-readable recording medium of claim 6, wherein the fixed time period is one week, and the peritoneal dialysis and hemodialysis hybrid-remedy planning program causes the computation unit to, in calculating a ratio M/C(0), calculate with respect to a schedule of the dialysis for the one week.

* * * * *